United States Patent [19]
>
> Hölzl

[11] Patent Number: 5,039,322

[45] Date of Patent: Aug. 13, 1991

[54] APPARATUS FOR EXTRACTING HOT GAS SAMPLES FROM A REACTION VESSEL

[75] Inventor: Kurt Hölzl, Sarleinsbach, Austria

[73] Assignee: Voest-Alpine Industrieanlangenbau Gesellschaft m.b.H., Linz, Austria

[21] Appl. No.: 296,220

[22] Filed: Jan. 10, 1989

[30] Foreign Application Priority Data

Jan. 11, 1988 [EP] European Pat. Off. ........ 88890003.2
Jan. 11, 1988 [EP] European Pat. Off. ........ 88890004.0

[51] Int. Cl.$^5$ ............................................. B01D 41/04
[52] U.S. Cl. ..................................... 55/302; 55/385.1;
73/863.24
[58] Field of Search ............... 422/50, 101; 73/863.24,
73/863.23; 55/302, 385.1; 134/37

[56] References Cited

U.S. PATENT DOCUMENTS

| | | | |
|---|---|---|---|
| 3,559,491 | 2/1971 | Thoen | 73/863.24 |
| 3,748,906 | 7/1973 | Manka | 73/863.01 |
| 3,759,087 | 9/1973 | Iwao et al. | 73/863.24 X |
| 4,161,883 | 7/1979 | Laird et al. | 73/863.24 |
| 4,578,986 | 4/1986 | Navarre | 73/863.24 X |
| 4,779,466 | 10/1988 | Ramsner et al. | 73/863.24 X |

FOREIGN PATENT DOCUMENTS

| | | |
|---|---|---|
| 95802 | 12/1983 | European Pat. Off. . |
| 219188 | 4/1987 | European Pat. Off. . |
| 243569 | 11/1987 | European Pat. Off. . |
| 243570 | 11/1987 | European Pat. Off. . |
| 2117796 | 10/1972 | Fed. Rep. of Germany . |
| 2301264 | 7/1974 | Fed. Rep. of Germany . |
| 3305232 | 8/1984 | Fed. Rep. of Germany . |
| 2363792 | 11/1976 | France . |

*Primary Examiner*—Richard L. Chiesa
*Attorney, Agent, or Firm*—Collard, Roe & Galgano,

[57] ABSTRACT

An apparatus for extracting hot gas samples from a reaction vessel has at least one extraction probe having a gas-conducting inner tube and a filter, which succeeds the extraction probe. The filter is composed of a filter cup and a filter plug disposed therein. To permit a simple cleaning of the filter, the filter cup is formed by a diametrically enlarged, coaxial extension of the inner tube of the extraction probe and the filter plug is carried by a filter bottom, formed with blast nozzles. The nozzles are directed into the annular space formed between the filter cup and the filter plug.

9 Claims, 2 Drawing Sheets

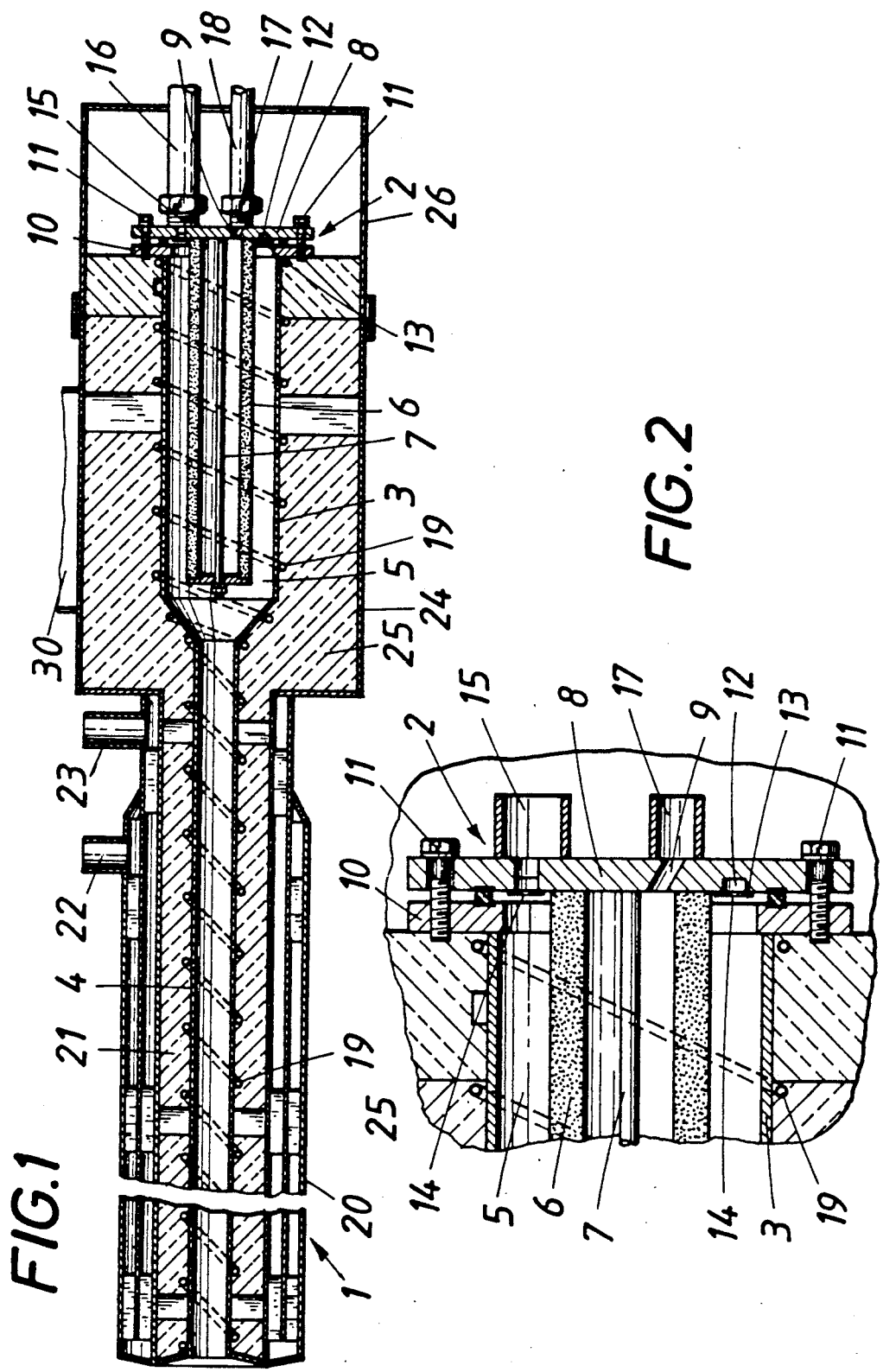

APPARATUS FOR EXTRACTING HOT GAS SAMPLES FROM A REACTION VESSEL

BACKGROUND OF THE INVENTION

1. Field of the Invention

This invention relates to an apparatus for extracting hot gas samples from a reaction vessel, which apparatus comprises at least one extracting probe having a gas-conducting heated inner tube, a cooled outer shell and heat insulation between the inner tube and the outer shell, and also comprises a filter, which succeeds the extracting probe and is composed of a filter cup and a filter plug, which is detachably inserted in the filter cup.

2. Description of the Prior Art

For a control of a reaction in dependence on the composition of hot gases produced by such reaction it is necessary to extract gas samples from the reaction vessel. Owing to the high gas temperatures the extracting probes used for that operation are provided with a cooled shell. But the action of such cooled shell may result in a temperature drop below the dew point temperature so that condensate may undesirably be formed in the inner tube of the extraction probe. Together with the dust content of the gas samples the condensate forms a sludge, which may deposit on the inner tube of the extraction probe and may constrict the flow area. In order to avoid a temperature drop below the dew point temperature it has already been proposed (EP-A-0 243 570) to provide the inner tube with heating means and to shield the inner tube from the cooled shell by heat insulation so that the otherwise occurring action of the cooled shell on the temperature of the inside surface of the inner tube will be prevented and the temperature of the inner tube can be kept in a desired range regardless of the temperature of the cooled shell. The dust which has been extracted with the gas sample must be separated from the gas sample by a filter, which succeeds the extracting probe and in which a temperature drop below the dew point temperature must also be avoided so that the filter will not be clogged by the dust which would be formed. Although heating means may be used for that purpose, a relatively expensive maintenance will be required in that case because the filter cup of the filter will be filled by the retained sludge and must be cleaned in regular intervals of time in that the filter plug is removed from the filter cup and is purged with compressed air and the dust which has been retained by the filter is manually removed from the filter cup.

Gas samples should be extracted from the reaction vessel also during such maintenance operations. For that purpose it is also known (EP-A-0 243 569) to provide two extracting probes, which are connected in parallel and through which the gas samples are extracted from the reaction vessel in alternation so that the required maintenance work can be performed at that extracting probe which is not used to extract gas at a time. In order to reduce the maintenance expenditure, more gas is extracted from the reaction vessel than is required for analysis and the surplus quantity of gas is blown through the respective other probe in a direction which is opposite to the extracting direction so that the filter associated with said other probe will be purged. But in spite of the fact that the filters are regularly purged in a direction which is opposite to the extracting direction, the dust which has been retained by the filter must be removed by hand from the filter cups because the repeated deflection of the purging streams will result in a formation of dead spaces in which dust can deposit.

In order to reduce the larger additional expenditure which is required for the connection of probes to the reaction vessel where two extraction probes are employed, it is also known (FR-A-2 363 792) to combine the extracting probes with a common air-cooled housing in a unit of construction. But that arrangement cannot reduce the expenditure involved in the maintenance work.

In connection with an extracting probe it is known (EP-A-0 219 188) to provide a filter cup which is constituted by a diametrically enlarged, coaxial extension of the inner tube of the extracting probe, so that the resulting decrease of the velocity of flow will promote the settling of the dust in the filter cup. But that feature does not eliminate the need for a manual cleaning of the filter cup even when the filter is purged in a direction which is opposite to the extracting direction. This is due to the fact that the purging air flowing through the filter plug can be used to substantially clean only the filter plug but cannot be used to clean the filter cup.

SUMMARY OF THE INVENTION

It is a first object of the invention so to improve an apparatus which is of the kind described first hereinbefore and serves to extract hot gas samples from a reaction vessel that the expenditure involved in the cleaning of the filter is considerably improved and the filter can be cleaned automatically.

It is a second object of the invention to accomplish the first object by the use of simple means.

The object set forth are accomplished in accordance with the invention in that the filter cup is constituted by a diametrically enlarged, coaxial extension of the inner tube of the extracting probe and is provided at its free end with a flange, which carries a detachably mounted filter bottom, which carries the filter plug and is provided with blast nozzles, which open into the annular space between the filter cup and the filter plug and are adapted to be connected to a blast line.

Because the filter cup is constituted by a coaxial extension of the inner tube of the extracting probe, the filter can be automatically cleaned as the dust which is retained in the annular space between the filter cup and the filter plug can be blown back from the filter cup through the inner tube of the extracting probe into the reaction vessel if the annular space between the filter cup and the filter plug is properly purged. Because such a stream of purging air stream is ensured by the blast nozzles provided at the filter bottom, that annular space can be completely cleaned without a residue. If the filter plug is purged too, as may be required, the filter need not be taken apart when it is to be cleaned.

A stream of purging air which is distributed over the cross-section of the annular space between the filter cup and the filter plug can be produced by simple means if the blast nozzles consist of blast openings, which are formed in the filter bottom and communicate with an annular channel.

The filter cup which is constituted by an extension of the inner tube of the extraction probe will usually be disposed outside the reaction vessel so that it will not be subjected to a temperature which requires a cooling of the filter. Nevertheless it is recommendable to provide a heat-insulated filter shell around the filter cup which is constituted by an extension of the inner tube of the extracting probe so that an unnecessary dissipation of heat to be supplied to the filter cup will be avoided.

Whereas the filter plug need not be removed from the filter cup for the regular maintenance of the filter, the filter cup must be accessible for such a removal of the plug. That requirement can be complied with in a simple manner in that the filter shell surrounding the filter cup has a detachable heat-insulated cover, which covers the filter bottom. In that case the ports for the blast line and the gas-delivering line may extend through said cover.

The apparatus in accordance with the invention can be used to special advantage for a continuous extraction of hot gas samples from a reaction vessel if two juxtaposed extraction probes are combined in a unit which is adapted to be connected to the reaction vessel and which comprises the two filters, which have at least substantially parallel axes and are constituted by extensions of the respective extraction probes. In that case the expenditure involved in the means for connecting two probes to the reaction vessel is reduced to the expenditure usually involved in the means for connecting one probe to said vessel and an automatic cleaning of both extraction probes will be ensured because each probe can be cleaned while samples are extracted through the respective other extraction probe. In that case the purging stream will be forced to flow parallel to the axis of the probe through the annular space between the filter cup and the filter plug because the purging stream need not be blown through the filter plug.

Each of the two extraction probes may be provided with a cooled outer shell for dissipating heat from the hot gases coming from the reaction vessel. Simpler conditions will be obtained, however, if the heated inner tubes of the two extraction probes are enclosed by a common cooled outer shell. In that case the heat insulation provided between the inner tubes and the common outer shell will prevent the cooled shell and the heated inner tubes from thermally influencing each other.

Just as the inner tubes of the extraction probes the heatable filter cups which are constituted by extensions of the inner tubes may be surrounded by a common heat-insulated shell which will reduce the dissipation of heat from the filter cups.

If two extraction probes are combined in a unit it will be possible to detect the gas temperature within the reaction vessel in a simple manner if a temperature sensor which protrudes into the reaction vessel is provided between the two extraction probes and indicates the gas temperature adjacent to the inner end portions of the two extraction probes protruding into the reaction vessel.

Particularly if the inner end portions of the extraction probes are straight, a purging stream flowing through one extraction probe might affect the composition of the gas samples which are being extracted through the other extraction probe. This can be avoided in that the inflowing and outflowing gas streams are separated in the reaction vessel by at least one guide wall, which is disposed between the inner tubes of the two extraction probes at their inner end portions, which protrude into the reaction vessel. Particularly desirable conditions will be obtained if a guide wall is associated with each inner tube and the temperature sensor protrudes into the reaction vessel between said guiding partitions. It need not be emphasized that the guide wall and/or the mounting and/or ports of the temperature sensor may also be provided with cooling means.

BRIEF DESCRIPTION OF THE DRAWING

FIG. 1 is a diagrammatic axial sectional view showing the apparatus in accordance with the invention used to extract hot gas samples from a reaction vessel by means of one extraction probe.

FIG. 2 is an enlarged sectional view showing the filter bottom of an apparatus as shown in FIG. 1.

DETAILED DESCRIPTION OF THE PREFERRED EMBODIMENTS

Figure 3:
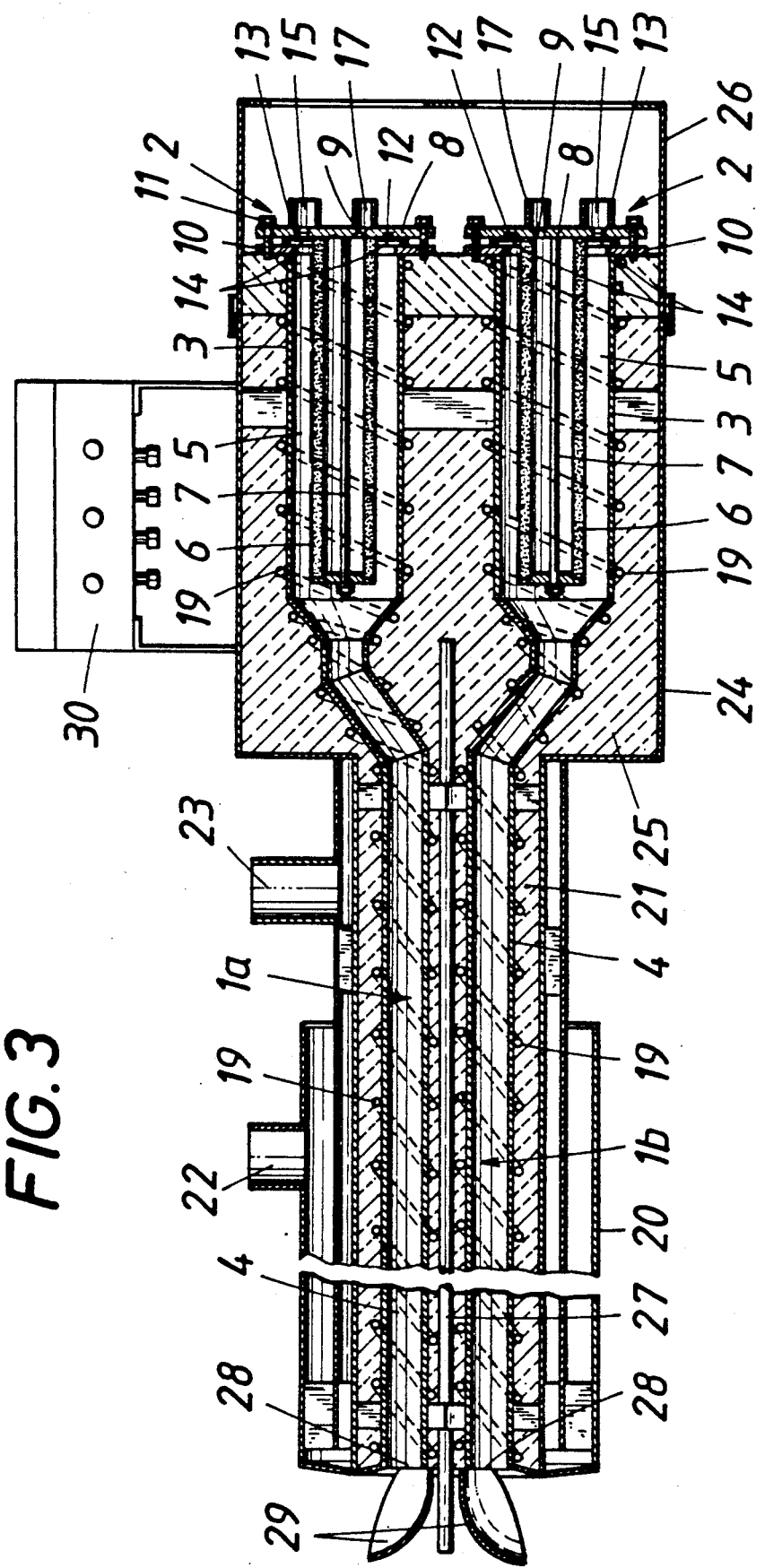
FIG. 3 is a simplified axial sectional view showing an apparatus in accordance with the invention for a continuous extraction of hot gas samples by means of two extraction probes.

Embodiments of the invention will now be described more in detail with reference to the drawing.

The apparatus shown in FIGS. 1 and 2 essentially consists of an extraction probe 1 and a succeeding filter 2, which comprises a filter cup 3 that is constituted by a diametrically enlarged, coaxial extension of the gas-conducting inner tube 4 of the extraction probe 1. The filtering medium is constituted by a filter plug 6, which is secured to the filter bottom 8 and protrudes into and defines an annular space 5 with the filter cup and is secured to the filter bottom 8 and by a clamp screw 7. Radially inwardly of the inside peripheral surface of the filter plug 6 the filter bottom 8 is formed with a gas exit opening 9. The filter bottom 8 is detachably secured to a mounting flange 10 of the filter cup 3 by means of screws 11 and adjacent to the annular space 5 is formed with an annular channel 12, which is covered toward the annular space 5 by a ring 13. The ring 13 is formed with an annular series of blast openings 14, which constitute blast nozzles, which are parallel to the axis of the filter cup 3. The annular channel 12 is connected to a blast line 16 by a tubular port 15, as is shown in FIG. 1. The gas exit opening 9 opens into a tubular port 17 connected to a gas-delivering line 18.

The inner tube 4 of the extraction probe 1 and the filter cup 3 of the filter 2 are surrounded by a heating coil 19 of an electric resistance heater, which is operable to prevent a temperature drop below the dew point temperature adjacent to the extraction probe 1 and the succeeding filter 2. The probe 1 and the filter 2 may be heated by separate heating coils or by a common heating coil.

Heat insulation 21 is provided between the inner tube 4 of the extraction probe 1 and the outer shell 20 of that probe. That heat insulation permits a control of the wall of the inner tube independently of the temperature of the outer shell 20, which is exposed to the hot gases within the reaction vessel and is provided with liquid cooling means. For that purpose the outer shell 20 is double-walled and is connected to a supply line 22 and a return line 23 for a liquid coolant.

Although the filter cup 3 is disposed outside the reaction vessel, the filter cup 3 is also surrounded by an outer filter shell 24 and heat insulation 25 is provided between the filter shell 24 and the filter cup 3. That heat insulation 25 will prevent an unnecessary dissipation of the heat that is to be supplied to the filter cup 3. The heat-insulated shell 24 is provided at its outer end with a cover 26, which has been fitted on and is removable from the shell 24 and covers the filter bottom 8. Heat insulation is provided in the cover 26 but is not shown for the sake of clearness.

The gas samples are extracted from the reaction vessel through the inner tube 4 of the extraction probe 1 and flow in the filter cup 3, in which they are sucked through the filter plug 6, and are then delivered to and in the gas line 18. The solids which have been removed from the gas sample in the filter are retained by and accumulated in the annular space 5 between the filter cup 3 and the filter plug 6 until a removal of dust from the filter 2 is required. Such a removal of dust is effected by means of a purging stream, which flows into the annular space 5 through the blast openings 14 and blows the accumulated dust through the inner tube 4 of the extraction probe back into the reaction vessel in a direction which is opposite to the delivery of gas from the filter cup 3. The filter plug 6 can be cleaned in that compressed gas from the gas line 18 is blown into the filter so that the filter plug 6 is purged too.

The extraction apparatus shown in FIG. 3 differs from that shown in FIGS. 1 and 2 in that the former comprises two juxtaposed parallel extraction probes 1a and 1b, each of which comprises an inner tube 4 for extracting gas. The two inner tubes 4 are surrounded by and constitute a unit with an outer shell 20, which at least in that portion which protrudes into the reaction vessel is double-walled and which is connected to a supply line 22 and with a return line for a liquid coolant. Heat insulation 21 is again provided between the outer shell 20 and the heated inner tube 4 to prevent the shell-cooling means and the means for heating the inner tubes from thermally influencing each other.

A temperature sensor 27 extending between the two inner tubes 4 and protruding into the reaction vessel and can be used to measure the temperature of the gas in the region in which the gas is extracted from the reaction vessel. The inner end portions 28 of the two inner tubes 4 are shielded from each other by two guide walls 29 and the temperature sensor 27 protrudes into the reaction vessel between two guide walls 29, by which the inner end portions 28 of the two inner tubes 4 are shielded from each other.

Just as in the embodiment shown in FIGS. 1 and 2, the embodiment shown in FIG. 3 comprises each of the extraction probes 1a and 1b of the embodiment shown in FIG. 3 is succeeded by a filter 2, which is constituted by an extension of the inner tube 4. The filters 2 are identical and serve to separate the dust which is entrained by the gas samples being extracted. The filter cups 3 are separately heated and are surrounded by a common outer shell 24, which is provided with heat insulation 25 so that energy supplied at a relatively low rate will be sufficient to prevent a temperature drop below the dew point temperature adjacent to the filter cups 3. The shell 24 is closed by a cover 26, which is formed with passages for the blast lines and for the gas-delivering lines. Said passages and lines are not shown for the sake of clearness.

The terminals for supplying electric power to the heaters, for the signal lines connected to the temperature sensor and for any control lines are combined in a terminal box 30.

In order to permit a continuous extraction of a gas sample from a reaction vessel, the gas sample is extracted from the reaction vessel through one of the two inner tubes, e.g., the inner tube of the extraction probe 1a, and the dust-laden gas is delivered to the succeeding filter 2, from which it is sucked through the filter plug 6 whereas the solid particles are retained in the annular space 5 between the filter cup 3 and the filter plug 6. The filter 2 which succeeds the other extraction probe 1b can be purged at the same time, preferably in that a surplus quantity of the gas which has been extracted through the extraction probe 1a is sucked back through the filter 2 and the inner tube 4 of the extraction probe 1b into the reaction vessel. That surplus gas is supplied to the filter 2 to be purged through a tubular port 15 for connection to the blast line and serves to blow dust from the filter cup 3 out of the latter and through the inner tube 4 of the extraction probe 1b into the reaction vessel. Because the filter 2 is constituted by an extension of the inner tube 4, the purging gas will flow along a substantially straight path without any deflection which would adversely affect the purging action. The filter plug 6 may also be purged in that composed gas is supplied to the filter 2 through the tubular port 17 connected to the gas line. The dust-laden gas stream flowing through the inner tube 4 of the extraction probe 1b cannot affect the composition of the gas sample which is extracted from the reaction vessel through the extraction probe 1a at the same time because the guide walls 29 ensure that the incoming and outgoing gas streams will be separated from each other.

When the quantity of solids which have accumulated in the filter cup 3 of the extraction probe 1a is so large that the satisfactory function of that filter 2 will be adversely affected, the extraction of gas is shifted from the extraction probe 1a to the extraction probe 1b and the filter 2 which is associated with the extraction probe 1a is purged in a direction which is opposite to the direction in which gas is extracted so that the filter 2 will be ready for use again when the filter 2 associated with the extraction probe 1b begins to be clogged. It is apparent that the extraction of gas through the two extraction probes 1a and 1b in alternation and the cleaning of said probes in alternation will permit a continuous analysis of gas for a control of the reaction in the reaction vessel.

I claim:

1. In an apparatus for extracting hot gas samples from a reaction vessel, comprising extraction probe means including a gas-conducting inner tube, heating means for heating said inner tube, outer shell means surrounding said inner tube, cooling means for cooling said outer shell means, and heat insulation between said inner tube and said outer shell means, and a filter, which is connected to said inner tube to receive gas therefrom and comprises a filter cup and a filter plug, which is detachably mounted in and defines an annular space with said filter cup, wherein the improvement comprises a diametrically enlarged coaxial extension of said inner tube and a flange at its end that is opposite to said inner tube, the extension and flange forming the filter cup, a filter bottom mounted on said flange and carrying said filter plug, and said filter bottom is formed with blast nozzles, which open into said annular space and are connected to a blast line.

2. The improvement set forth in claim 1, wherein said blast nozzles consist of blast openings formed in said filter bottom and said filter bottom is provided with an annular channel, which communicates with all said blast nozzles.

3. The improvement set forth in claim 1, wherein said extension of said inner tube is surrounded by a heat-insulated filter shell.

4. The improvement set forth in claim 3, wherein said filter shell is provided with a detachably mounted, heat-insulated cover, which covers said filter bottom.

5. The improvement set forth in claim 1, wherein
said extraction probe means comprises two extraction probes including two of said inner tubes, which are juxtaposed and together with said heating means, outer shell means, cooling means and heat insulation are combined to form a unit, which is connected to said reaction vessel, and
said unit also comprises two of said filters, which are juxtaposed and have at least substantially parallel axes and are connected to respective ones of said inner tubes.

6. The improvement set forth in claim 5, wherein said outer shell means consists of a common outer shell, which surrounds both of said inner tubes and is provided with cooling means.

7. The improvement set forth in claim 5, wherein said filter cups are surrounded by a common heat-insulated filter shell.

8. The improvement set forth in claim 5, comprising a temperature sensor which extends between said two inner tubes and protrudes into said extraction vessel.

9. The improvement set forth in claim 5, wherein
each of said inner tubes comprises opposite to the associated filter an end portion protruding into said reaction vessel,
said apparatus is operable to extract hot gas samples from said reaction vessel through one of said inner tubes so as to form in said reaction vessel an outflowing gas stream flowing into said end portion of said one inner tube and to blow dust-laden purging gas from said blast line through the other of said inner tubes into said reaction vessel so as to form in said reaction vessel an inflowing gas stream flowing out of said end portion of said other inner tube, and
at least one guide wall for shielding said outflowing and inflowing gas streams from each other is provided in said reaction vessel between said end portions.

* * * * *